United States Patent [19]

Yamaguchi et al.

[11] Patent Number: 5,230,634

[45] Date of Patent: Jul. 27, 1993

[54] PROTECTOR FOR MOUNTING ON LEADING CORD CHIP

[75] Inventors: Kimio Yamaguchi; Takeshi Yushiya; Koichi Mizoi; Chuji Shimizu, all of Tokyo, Japan

[73] Assignee: Fukuda Denshi Co., Ltd., Tokyo, Japan

[21] Appl. No.: 798,578

[22] Filed: Nov. 26, 1991

[30] Foreign Application Priority Data

Jun. 18, 1991 [JP] Japan .................... 3-054458[U]

[51] Int. Cl.⁵ ............... H01R 13/44; H01R 13/64; A61B 5/04
[52] U.S. Cl. ................... 439/149; 439/909; 128/639; 128/643
[58] Field of Search ............ 439/134, 149, 909, 137, 439/141; 128/783, 639, 640, 644, 798, 802, 643

[56] References Cited

U.S. PATENT DOCUMENTS 3,602,216 8/1971 Moe, Jr. .................. 128/640
4,632,121 12/1986 Johnson et al. .......... 128/639
4,806,112 2/1989 Roberts et al. .......... 439/149

Primary Examiner—Lee S. Cohen
Assistant Examiner—Marianne Parker
Attorney, Agent, or Firm—Sughrue, Mion, Zinn, Macpeak & Seas

[57] ABSTRACT

A protector for being mounted on a leading cord chip, and which is fixable to the top portion 1A of a leading cord fixing portion 1, includes an insulated cover portion which is longer than a conductive plug 2 projecting from the top portion 1A. The insulated cover portion has a slit through which only a connecting portion of an electrode can pass. The connecting portion of the electrode is connected to the plug 2.

9 Claims, 5 Drawing Sheets

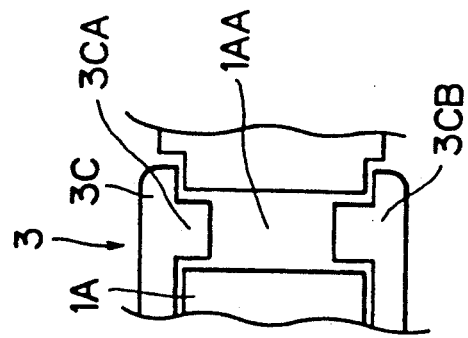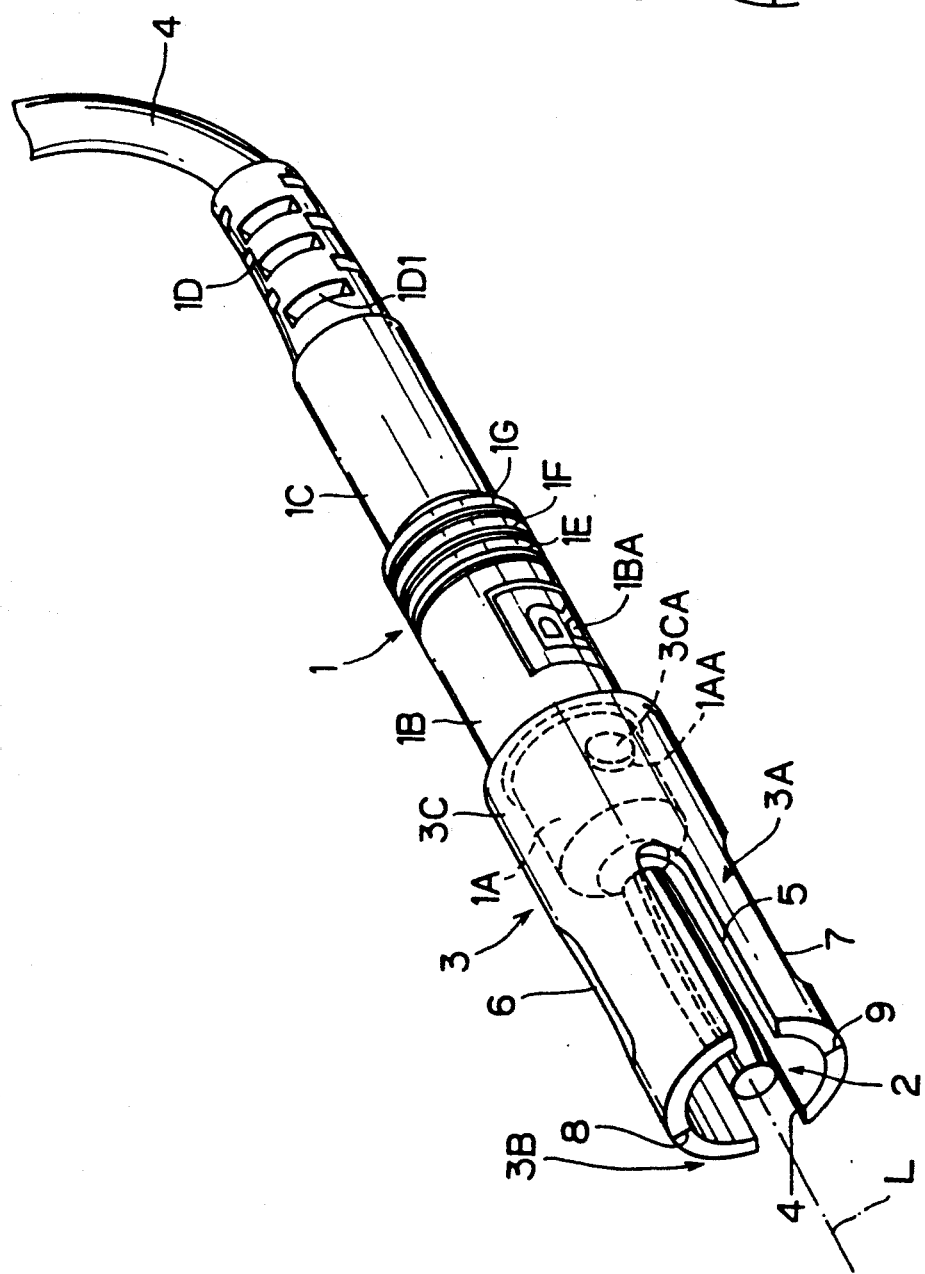

PROTECTOR FOR MOUNTING ON LEADING CORD CHIP

BACKGROUND OF THE INVENTION

The present invention relates to a protector for mounting on a leading cord chip. More particularly, it relates to a protector for mounting on the leading cord chip in which an operator's fingers or the like cannot contact a plug projecting from the top of the leading cord chip.

Generally, a leading cord chip is a connecting portion mounted on the top of the leading cord, which is connected with an electrode or another apparatus. The above leading cord is a cord through which an electrocardiogram signal from a patient is conveyed. The conventional leading cord chip has a metallic plug 11 projecting from the top thereof, as shown in FIG. 1A. A leading cord 13 is connected to the plug 11, which protrudes through a shell 12.

Methods for using the leading cord chip are as follows.

One method connects the plug 11 with a durable electrode which is not disposable but which is usable for a relatively long time. For example, the electrode may be a band-type limb electrode or an absorption-type breast electrode. The electrode connects the leading cord 13 with an electrocardiograph.

On the contrary, another method connects the leading cord 23 with a disposable electrode, for example, a magnet-type breast electrode, and connects the plug 11 with the relay portion of a cord connected with the electrocardiograph.

In both of the above-described methods, the electrocardiogram signal, which is led from the patient through the electrode, is input into the electrocardiograph device through the leading cord chip, as shown in FIG. 1A, whereby the electrocardiogram signal is input accordingly.

However, in the leading cord chip shown in FIG. 1A, the following problem results. That is, since the plug 11 is exposed, it may be inserted erroneously into the female pin 21A of a connector 21, etc. connected to a commercial electric power source.

To solve the above problem, as shown in FIG. 1B, a protector 30 has been provided having two cover portions 30A and 30B which are situated at both sides of a plug 20 projecting from a cord fixing portion 10.

With the protector 30, it is impossible to insert the plug 20 erroneously into the female pin 21A of a connector 21 of a commercial electric power source. Consequently, the protector 30 avoids the potential problem of current flowing into the patient through the plug 20.

However, since the interval between the cover portions 30A and 30B is relatively large, the protector 30 has the following problem. That is, fingers, etc. of the operator, patient, etc. may contact the plug 20 through the cover portions 30A and 30B. Consequently, the operator is exposed to the current. For example, when electrocardiogram signal is output by a band-type limb electrode or an absorption-type breast electrode, all the leading cords are not always used.

Hence, some of the leading cord chips are not used. In this case, when the operator's finger contacts one of the leading unused cord chips, the finger enters the chip through the cover portions 30A and 30B. As a result, the operator's finger contacts the plug 20, as shown in the left drawing of FIG. 1C.

Further, many electrical apparatuses (i.e., a computer, air conditioner, freezer, etc.) are placed in the patient's room. These electrical apparatuses and medical instruments of the above-mentioned electrocardiograph, etc. are commonly grounded. Moreover, standards on voltage or current, etc. are not uniform between the above-mentioned electric apparatuses and the medical instruments. Accordingly, leakage current from the electric apparatuses may be input into the plug 20 along the patient's body, and may enter the patient through the leading cord chip.

Further, the plug 20 contacts the iron frame 40 of a bed (as shown in the central drawing of FIG. 1C), or the plug 20 contacts the corner of a metallic desk 50 (as shown in the right drawing of FIG. 1C). In the above-described cases, leakage current from the electric apparatuses may be input to the plug 20 along the iron frame 40 or the metallic desk 50, whereby it enters a patient through the leading cord chip being used.

SUMMARY OF THE INVENTION

An object of the present invention is to ensure that the protector mounted on the top portion of the leading cord chip is safe and that the plug cannot contact the patient or operator.

The above-mentioned object can be achieved by a protector for mounting on the leading cord chip, which is fixable to the top portion 1A of a leading cord fixing portion 1. The protector comprises an insulated cover portion which is longer than a conductive plug 2 projecting from the top portion 1A, the insulated cover portion having a slit through which only a connecting portion of an electrode may pass. The connecting portion of the electrode is connected to the plug 2.

BRIEF DESCRIPTION OF THE DRAWINGS

Further features and advantages of the present invention will be apparent from the description below with reference to the accompanying drawings, wherein:

FIGS. 2A to 2B generally illustrate an embodiment of the present invention;

DESCRIPTION OF THE PREFERRED EMBODIMENTS

Figure 1A:
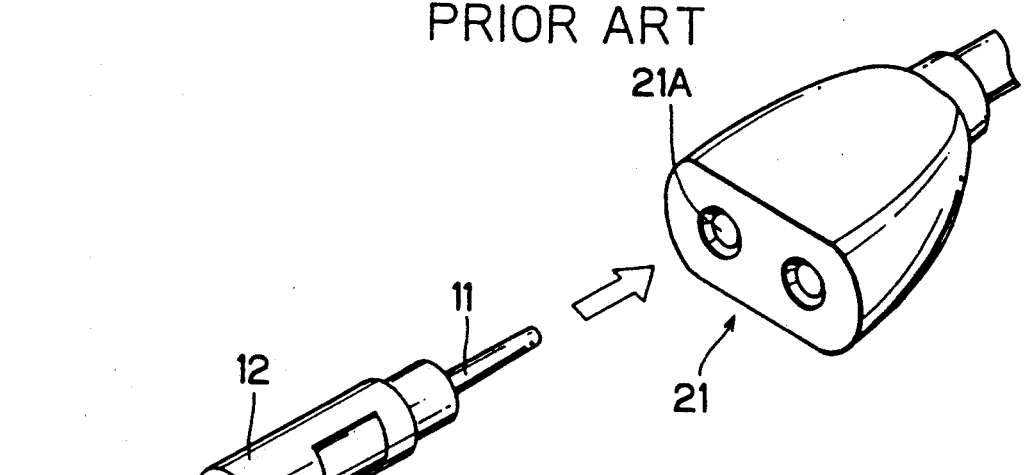
FIGS. 1A to 1C illustrate a conventional protector.
Figure 1B:
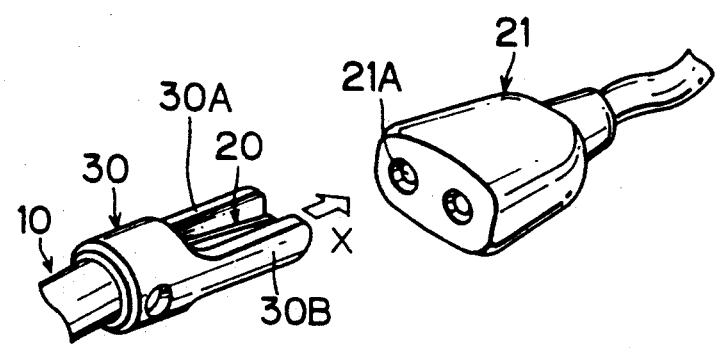
Figure 1C:
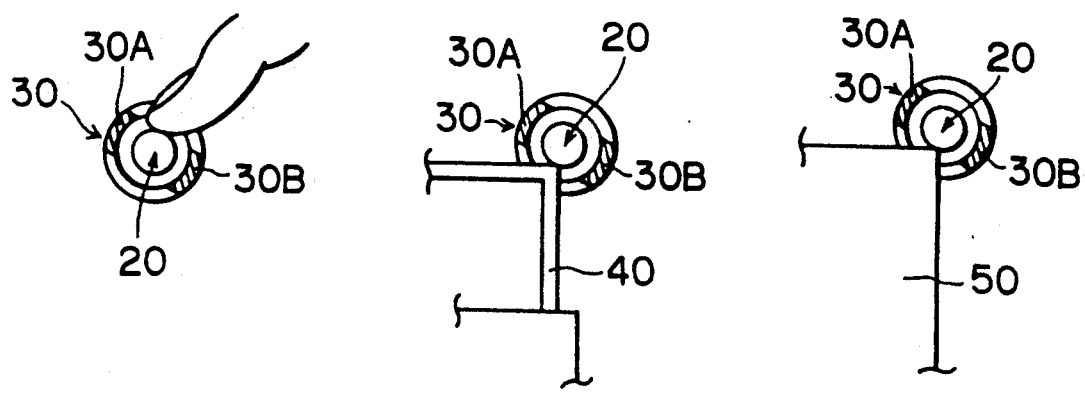

FIGS. 2A to 2B generally illustrate an embodiment of the present invention.

Referring to FIGS. 2A and 2B, reference numeral 1 designates a leading cord fixing portion, 2 is a plug, 3 is a leading cord chip protector, and 4 and 5 are slits.

The leading cord fixing portion is insulated, and is formed, for example, of plastics. The fixing portion has a substantially cylindrical shape through which a leading cord 4 extends and is fixed. The leading cord fixing portion 1 includes a top portion 1A, a central portion 1B and a base portion 1C. Annular projections 1E, 1F, and 1G are arranged between the central portion 1B and the base portion 1C, so that when the leading cord fixing portion 1 is gripped by the operator's hands, the annular projections do not slip along the portion 1.

To the rear of the base portion 1C of the fixing portion 1, a fastening portion 1D for fastening the leading cord 4 is integrated with the base portion 1C and a plurality of crevices 1D1 are formed, whereby the leading cord 4 can bend easily.

An identification symbol 1BA is inscribed on the central portion 1B of the leading cord fixing portion 1. In the identification symbol 1BA shown in FIG. 2A, for example, the letter "R" is inscribed to indicate a right-handed arrangement.

The top portion 1A of the leading cord fixing portion 1 has a cylindrical shape and a diameter smaller than that of the central portion 1C, and the conductive plug 2 projects from portion 1A. The leading cord 4 is connected to the plug 2. The plug 2 may be a so-called "banana-type", in which the center is relatively thick and resilient. Alternatively, the plug 2 may be a so-called "solid-type" in which the entire plug 2 has a cylindrical shape.

On the top portion 1A of the leading fixing portion 1, the leading cord chip protector 3 in accordance with the present invention is fixed. The leading cord chip protector 3 has a substantially cylindrical shape and is insulated, and either may be integrated with the top portion 1A of the leading cord fixing portion 1, or may be formed by material different from the top portion 1A, e.g., plastics.

The protector 3 has a cylindrical base portion 3C, and first and second cover portions 3A and 3B integrated with the cylindrical base portion 3C. As mentioned above, the base portion 3C of the protector 3 may be integrated with the top portion 1A of the leading cord fixing portion 1. Alternatively, the base portion 3C may be mounted on the top portion 1A, as shown in FIG. 2B, wherein projections 3CA and 3CB are formed on the inside surface of the base portion 3C, and which are engageable with a through hole 1AA of the top portion 1A.

Through engagement of the projections 3CA and 3CB with the through hole 1AA, the protector 3, in accordance with the present invention, may be fixed to the top portion 1A of the leading cord fixing portion 1. The cover portions 3A and 3B are placed at both sides of the plug 2 and are longer than the plug 2, as shown in FIG. 2A.

Figure 5A:
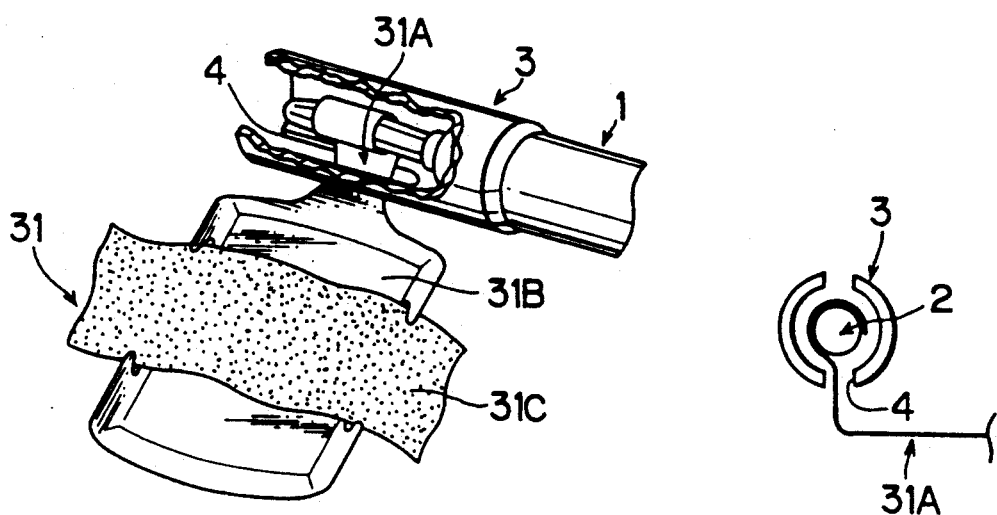
FIGS. 5A to 5C are views illustrating the operation of the present invention.
Figure 5B:
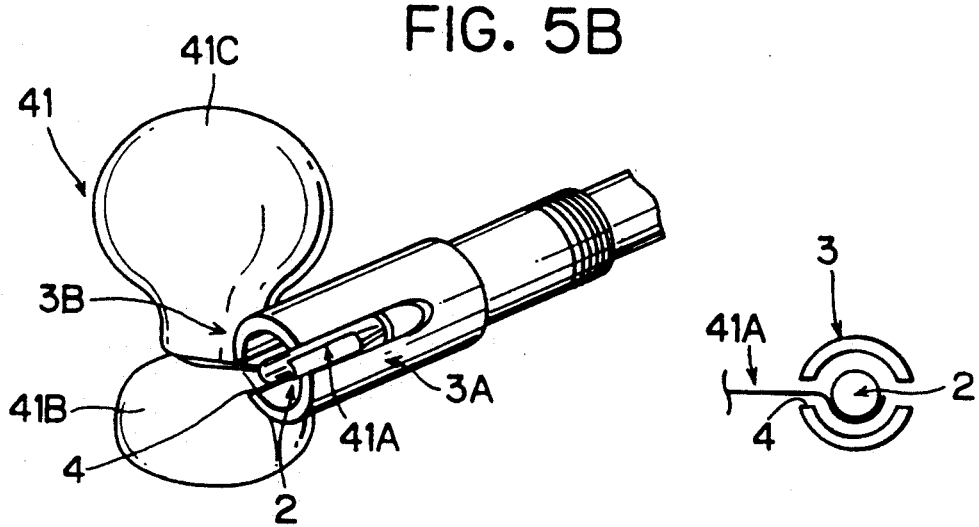

A slit is formed on the cover portions 3A and 3B, through which only a leading cord chip connecting portion 31A or 41A, as shown in FIG. 5A or 5B, may pass. The connecting portion 31A or 41A is connected to the plug 2.

Figure 3A:
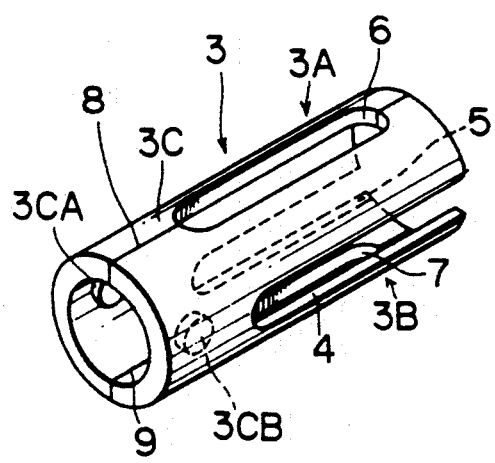
FIGS. 3A to 3C and FIGS. 3D to 3F, respectively, illustrate in detail first and second embodiments of the present invention.
Figure 3D:
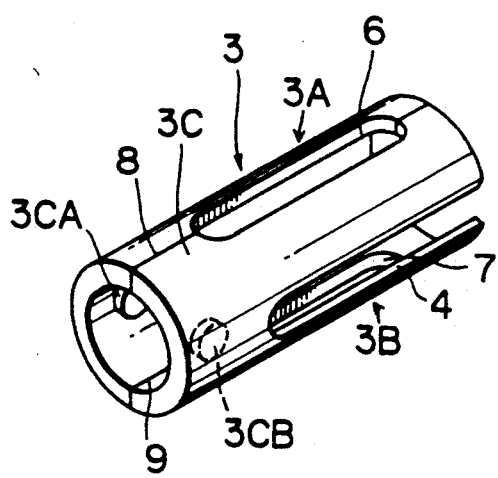
Figure 3B:
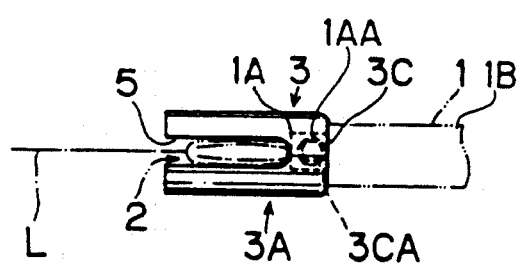
Figure 3E:
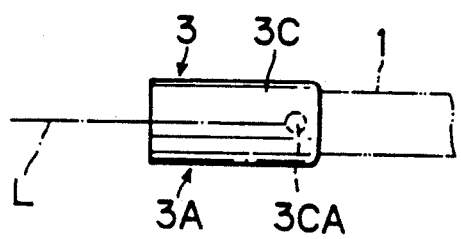
Figure 3C:
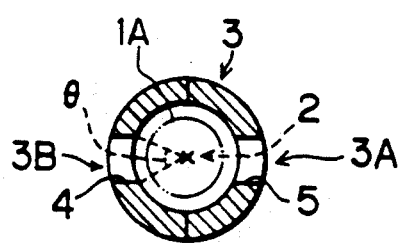
Figure 3F:
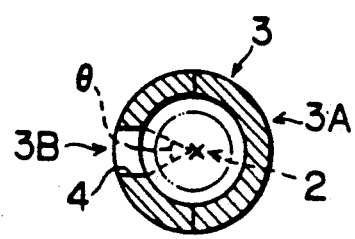

FIGS. 3A to 3C show an example of a protector having two slits, while FIGS. 3D to 3F show an example of a protector having only one slit. The difference between the embodiment of FIGS. 3A14 3C and that of FIGS. 3D-3F is as follows. That is, in the case of two slits, namely, slits 4 and 5(see FIGS. 3A to 3C), the plug 2 can be viewed through the slit 5, as shown in FIG. 3B.

On the contrary, when the protector has only one slit, namely, only the slit 4 (see FIGS. 3D to 3F), the plug 2 cannot be observed as shown in FIG. 3E.

Figure 5C:
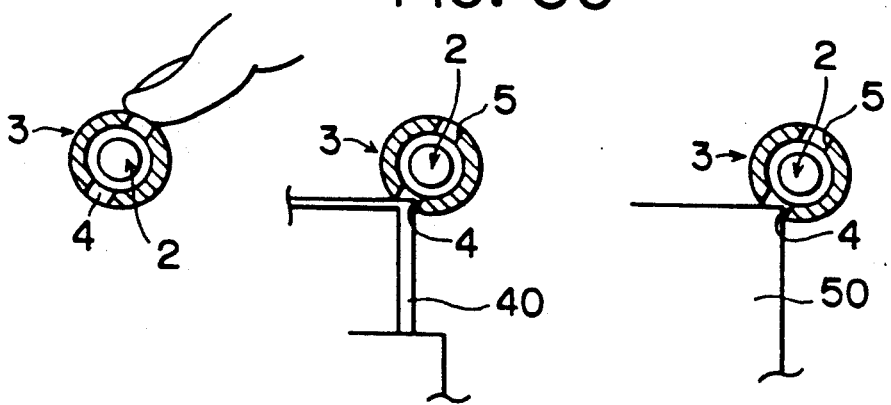

Preferably, the angle $\theta$, formed by the center of the plug 2 and the slit, is smaller than 90°, as shown in FIGS. 3C and 3F. As a result, the plug 2 does not contact the operator's fingers or an iron frame 40 of a bed or the corner of a metallic desk 50, each having an angle of 90°, as shown in FIGS. 5C. Moreover, preferably openings 6 and 7 are formed parallel to the slit, as shown in FIG. 2A, 3A and 3D. The length of the openings 6 and 7 is slightly shorter than that of the slit, as shown in FIG. 2A. The openings 6 and 7 are provided for the following reasons.

First, when the protector 3 is connected to the connecting portion 31A (see FIG. 5A) or 41A (see FIG. 5B), the connection may be confirmed by observing the plug 2 through the openings 6 and 7. Additionally, the protector 3 becomes lightweight due to the openings 6 and 7 provided in the protector.

Figure 4A:
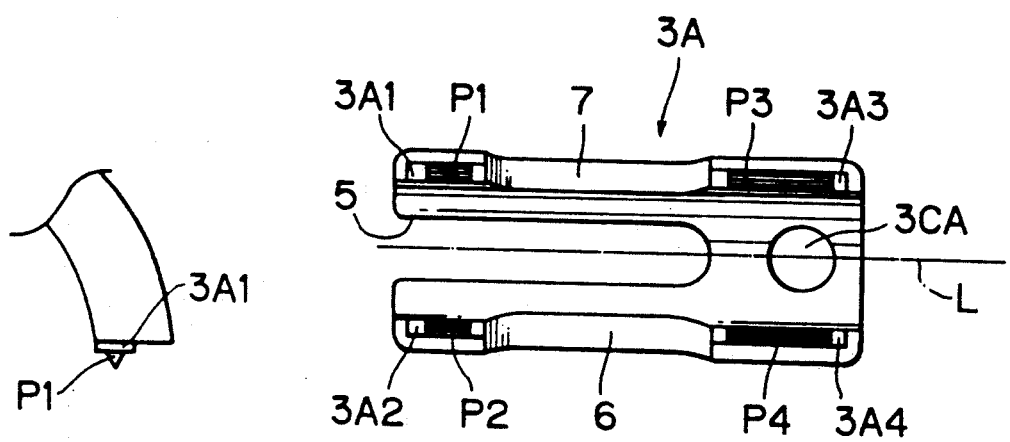
FIGS. 4A to 4B are exploded views of another embodiment of the present invention.
Figure 4B:
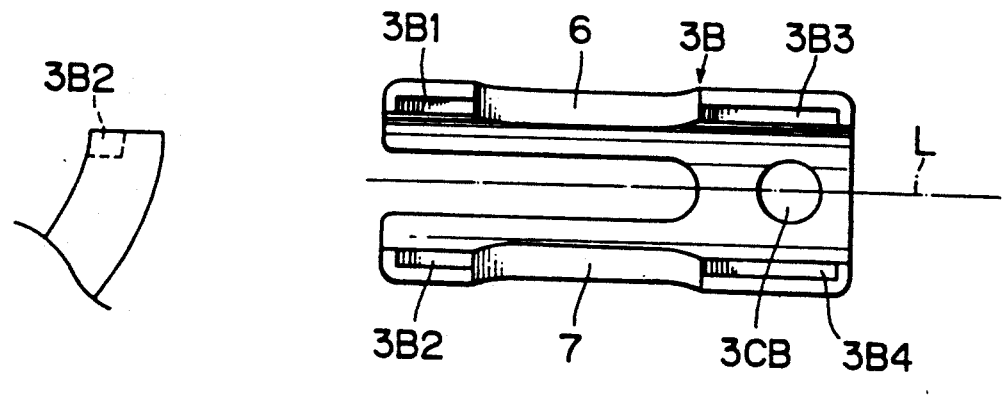

On the other hand, the first and second cover portions 3A and 3B may be integrated with each other, or, alternatively, they may be joined together by supersonic welding, as shown in FIGS. 4A and 4B which show the structure of the first and second cover portions 3A and 3B, respectively. Since the cover portions 3A and 3B are joined together on the inner surfaces on which the openings 6 and 7 are provided, joints 8 and 9 are exposed at both sides of the openings 6 and 7 on the outer surfaces of the protector 3, as shown in FIGS. 2A, 3A, and 3D.

Referring to FIG. 4A, locating convex portions 3A1, 3A2, 3A3, and 3A4, and supersonic welding projection portions P1, P2, P3 and P4 are formed on the first cover portion 3A.

On the other hand, referring to FIG. 4B, locating concave portions 3B1, 3B2, 3B3, and 3B4, corresponding to the convex portions 3A1, 3A2, 3A3, and 3A4, are formed on the second cover portion 3B.

Based on the above-described structure, the cover portions 3A and 3B can be tentatively joined together by inserting the locating convex portions 3A1 to 3A4 of the first cover portion 3A into the corresponding locating concave portions 3B1 to 3B4 of the second cover portion 3B, respectively. Thereafter, supersonic welding is performed so that the projections P1 to P4 and the concave portions 3B1 to 3B4 are welded together, respectively. Accordingly, the first and second cover portions 3A and 3B may be secured together.

The operation of the present invention having the above structure will be explained hereinafter, based on FIGS. 5A to 5C. For convenience, the present invention will be applied to the durable electrode comprising either the band-type limb electrode (see FIG. 5A) or the absorption-type breast electrode (see FIG. 5B). However, the present invention is not restricted to the above-mentioned types of electrodes, and indeed may also be applied to the disposable electrode of the magnet-type breast electrode, etc.

It is well known that the band-type limb electrode 31, as shown in FIG. 5A, is used when the electrocardiogram is produced and output by winding a band 31C mounted on a electrode plate 31B along the limbs, for example, a wrist, of a patient. A leading cord chip connecting portion 31A is provided on the electrode plate 31B of the electrode 31, as shown in FIG. 5A. A slit 4 of the protector 3, in accordance with the present invention, is brought to the connecting portion 31A, and the connecting portion 31A is inserted in the slit 4. Thus, the connecting portion 31A is made to pass through the slit 4, whereby the plug 2 may be connected with the connecting portion 31A. Hence, the electrocardiogram signal is led from the patient, and is input to an electrocardiograph device by the leading cord 4 extending from the fixing portion 1 as shown in FIG. 2A, and is processed accordingly.

It is well known that, when the absorption-type breast electrode 41, as shown in FIG. 5B, is used, a metallic cup 41B may be mounted on the patient's breast by suction by manually operating a rubber ball 41C. The metallic cup 41B also functions as the electrode. Therefore, when the plug 2 is connected to the connecting portion 41A joined to the cup 41B, the electrocardiogram signal may be output from the patient.

The method for connecting the plug 2 to the connecting portion 41A is similar to that shown in FIG. 5A. That is, a slit 4 of the protector 3, in accordance with the present invention, is brought to the connecting portion 41A, and the connecting portion 41A is inserted in the slit 4. Thus, the connecting portion 41A passes through the slit 4, whereby the plug 2 is connected to the connecting portion 41A.

As mentioned above, in accordance with the present invention, the slit is formed on the cover portion, and only the connecting portion of the electrode connected to the plug 2 passes through the slit. Thus, as shown in FIG. 5C, an operator's finger (e.g., see the left drawing), the iron frame 40 of a bed (e.g., see the central drawing), or the corner of a metallic desk 50 (e.g., see the right drawing), do not contact the plug 2. Instead, only the connecting portions 31A and 41A contact the plug. Accordingly, the protector 3 ensures the safety of the operator, the patient, etc.

As mentioned above, according to the present invention, as shown in FIG. 2A, a protector is mounted on the leading cord chip, and is fixedly secured to the top portion 1A of a leading cord fixing portion 1. The protector comprises an insulated cover portion which is longer than a conductive plug 2 projecting from the top portion 1A. The insulated cover portion has at least one slit through which only a connecting portion of an electrode may pass, the connecting portion of the electrode being connected to the plug 2.

Thus, according to the above-described structure, the insulated cover portion has the slit formed thereon, and only the connecting portion of the electrode connected to the plug 2 may pass through the slit, as shown in FIGS. 5A and 5B.

Accordingly, as shown in FIG. 5C, the protector according to the invention is different from the conventional structure in that the patient's or operator's fingers etc., are prevented from contacting the plug 2. Instead, only the connecting portion of the electrode may contact the plug. Hence, leakage current nearby the electric apparatuses will not be input into the patient through an unused leading cord chip. Thus, according to the invention, the protector mounted on the leading cord chip prevents the plug from being erroneously and dangerously contacted.

We claim:

1. A protector for use with an electrode and for mounting on a leading cord chip having a conductive plug and a leading cord fixing portion, said protector being fixable to a top portion of the leading cord fixing portion, and said conductive plug projecting from said top portion, said protector comprising:
    an elongated insulative cover for receiving said conductive plug projecting from said top portion, said insulated cover having a length greater than that of said conductive plug, said insulated cover having a slit through which only a connecting portion of said electrode can pass,
    said connecting portion of the electrode adapted to be connected to said plug, said protector further comprising means, positioned in said cover, for allowing observation of the plug through said cover.

2. A protector for use with an electrode and for mounting on a leading cord chip having a conductive plug and a leading cord fixing portion, said protector being fixable to a top portion of the leading cord fixing portion, and said conductive plug projecting from said top portion, said protector comprising:
    an elongated insulative cover for receiving said conductive plug projecting from said top portion, said insulated cover having a length greater than that of said conductive plug, said insulated cover having a slit through which only a connecting portion of said electrode can pass,
    said connecting portion of the electrode adapted to be connected to said plug,
    wherein said top portion has a cylindrical shape and includes a through hole therein, said protector further comprising a cylindrical base portion corresponding to said top portion, and projections formed on an inner surface of the base portion and engageable with said through hole of said top portion.

3. A protector for use with an electrode and for mounting on a leading cord chip having a conductive plug and a leading cord fixing portion, said projector being fixable to a top portion of the leading cord fixing portion, and said conductive plug projecting from said top portion, said protector comprising:
    an elongated insulative cover for receiving said conductive plug projecting from said top portion, said insulated cover having a length greater than that of said conductive plug, said insulated cover having a slit through which only a connecting portion of said electrode can pass,
    said connecting portion of the electrode adapted to be connected to said plug,
    wherein said cover includes a plurality of openings for allowing observation of said plug therethrough, said openings being formed parallel to said slit.

4. A protector according to claim 1, wherein said cover comprises a first cover portion and a second cover portion, said first and second cover portions being joined together.

5. A protector according to claim 4, wherein said first and second cover portions are joined together by supersonic welding.

6. A protector according to claim 5, further comprising convex portions and welding projection portions formed on said first cover portion, and concave portions, corresponding to said convex portions, formed on said second cover portion.

7. A protector for use with an electrode and for mounting on a leading cord chip having a conductive plug and a leading cord fixing portion, said protector being fixable to a top portion of the leading cord fixing portion, and said conductive plug projecting from said top portion, said protector comprising:
    an elongated insulative cover for receiving said conductive plug projecting from said top portion, said insulated cover having a length greater than that of said conductive plug, said insulated cover having a plurality of slits through which only a connecting portion of said electrode can pass,
    said connecting portion of the electrode adapted to be connected to said plug.

8. A protector according to claim 1, wherein only one slit is formed on said cover.

9. A protector for use with an electrode and for mounting on a leading cord chip having a conductive plug and a leading cord fixing portion, said protector being fixable to a top portion of the leading cord fixing portion, and said conductive plug projecting from said top portion, said protector comprising:

an elongated insulative cover for receiving said conductive plug projecting from said top portion, said insulated cover having a length greater than that of said conductive plug, said insulated cover having a slit through which only a connecting portion of said electrode can pass, said connecting portion of the electrode adapted to be connected to said plug, wherein said slit in said cover includes first and second edges of said cover, and wherein an angle $\theta$, formed by a center of the plug and said first and second edges of said cover defining the slit, is smaller than 90 degrees.

* * * * *